United States Patent
Hughes et al.

(10) Patent No.: US 7,346,144 B2
(45) Date of Patent: Mar. 18, 2008

(54) IN VIVO PLANNING AND TREATMENT OF CANCER THERAPY

(75) Inventors: John H. Hughes, Martinez, CA (US); Juan Carlos Celi, Martinez, CA (US); Francisco Miguel Hernandez-Guerra, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/099,115

(22) Filed: Mar. 14, 2002

(65) Prior Publication Data

US 2003/0174808 A1   Sep. 18, 2003

(51) Int. Cl.
*A61N 5/10* (2006.01)

(52) U.S. Cl. .......................... 378/65; 378/64

(58) Field of Classification Search ............ 378/65, 378/64

See application file for complete search history.

(56) References Cited

U.S. PATENT DOCUMENTS

| | | | | |
|---|---|---|---|---|
| 3,955,089 A * | 5/1976 | McIntyre et al. | ............ | 378/65 |
| 4,118,631 A * | 10/1978 | Froggatt | ............ | 378/65 |
| 4,365,341 A * | 12/1982 | Lam | ............ | 378/65 |
| 4,695,731 A * | 9/1987 | Larkin | ............ | 250/374 |
| 4,815,448 A * | 3/1989 | Mills | ............ | 600/2 |
| 5,329,567 A * | 7/1994 | Ikebe | ............ | 378/65 |
| 5,621,779 A | 4/1997 | Hughes et al. | ............ | 378/65 |
| 5,754,622 A * | 5/1998 | Hughes | ............ | 378/65 |
| 5,870,697 A * | 2/1999 | Chandler | ............ | 378/65 |
| 6,301,329 B1 * | 10/2001 | Surridge | ............ | 378/65 |
| 6,385,286 B1 * | 5/2002 | Fitchard et al. | ............ | 378/65 |
| 6,519,316 B1 * | 2/2003 | Collins | ............ | 378/65 |
| 6,714,620 B2 * | 3/2004 | Caflisch et al. | ............ | 378/65 |

OTHER PUBLICATIONS

Zhu et al., "Portal dosimetry using a liquid ion chamber matrix: Dose response studes", Medical Physics, vol. 22, No. 7, Jul. 1995, pp. 1101-1106.*

* cited by examiner

*Primary Examiner*—Chih-Cheng G Kao

(57) ABSTRACT

A system and method for delivering radiation to an object. A computer tomography machine generates CT data of the object. A radiation source with an output beam is directed to a predetermined irradiation field of the object. A detector above the object controls the output beam to the predetermined irradiation field of the object. A processor calculates the dose to the predetermined irradiation field of the object. Another detector below the object which measures the radiation delivered to the object.

4 Claims, 5 Drawing Sheets

IN VIVO PLANNING AND TREATMENT OF CANCER THERAPY

BACKGROUND OF THE INVENTION

Description of the Related Art

Radiation-emitting devices are generally known and used, for instance, as radiation therapy devices for the treatment of patients. A radiation therapy device generally comprises a gantry, which can be swiveled around a horizontal axis of rotation during the course of therapeutic treatment. A linear accelerator is located in the gantry for generating high-energy radiation beam (typically, of electrons or photons, that is, X-rays) for therapy. During treatment, this radiation beam is trained on a zone of a object located in the isocenter of the gantry rotation. Radiation treatment devices have built in safety schemes that give the user confidence that the correct radiation is being delivered. However, it is hard to guarantee the delivery of radiation to the treatment site.

Before treatment, an object (e.g., a patient) may be scanned with a computer tomograph (CT), and/or treatment may be simulated with a diagnostic X-ray unit (i.e., a simulator). These devices identify the area in the body to be irradiated and the surrounding critical organs. The physician determines a method of treatment based on the patient's weight and age, along with the type and size of the diseased area. The treatment plan also calculates the radiation exposure to healthy tissue. The physician approves the plan, which is then transferred to the radiation-emitting device.

Data from the CT and/or the simulator along with the radiation emitting device data are used in the treatment planning process to calculate the dose levels in monitor units (MUs), which are to be delivered to the treatment site. MUs must be calibrated to a known reference setup. An MU is a unit of radiation from which the absorbed dose can be calculated. One MU is normally calibrated to 1 centiGray (cGy). The number of MUs is set at the console of a linac in order to deliver a prescribed dose of radiation. The linac is controlled with integrated detectors (e.g., ionization chambers). The detectors measure the amount of radiation generated by the linac, but not the actual radiation delivered to the targeted segment. Each day, when the treatment is delivered, the machine setup and dose values are recorded, either manually or automatically. However, the actual amount of radiation inside the object is unknown.

To control the radiation emitted toward an object, an aperture plate arrangement is usually provided in the trajectory of the radiation beam between the radiation source and the object. This aperture plate arrangement defines a field on the object to which the prescribed radiation is to be delivered. A wedge-shaped radiation distribution can be achieved by introducing, for example, a wedge-shaped absorption filter or a virtual wedge comprising aperture plates, which are moving during the irradiation. Such devices, however, modify the actual radiation delivered to the object in a predicted manner. Unfortunately, these devices have no way of determining how much radiation has been deposited to the object because the object may be in a wrong position. Instead, the amount of radiation measured was the amount of radiation generated by the linac, and not the actual radiation delivered to the object.

During dynamic conformal treatments, the gantry, collimator, jaws and/or multileaf collimators could all be in motion during the radiation treatment. When this occurs, it is even more difficult to verify whether the correct amount of radiation has been delivered to the treatment site because the treatment site lacks monitoring capability. The accelerator's dynamic motions have an impact on the amount of radiation delivered to the object. This impact can be predicted, but cannot be measured because of the object's possible movement.

SUMMARY OF THE INVENTION

A system and method for delivering radiation to an object. A computer tomography machine generates CT data of the object. A radiation source with an output beam is directed to a predetermined irradiation field of the object. A detector above the object controls the output beam to the predetermined irradiation field of the object. A processor calculates the dose to the predetermined irradiation field of the object. Another detector below the object which measures the radiation delivered to the object.

DETAILED DESCRIPTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
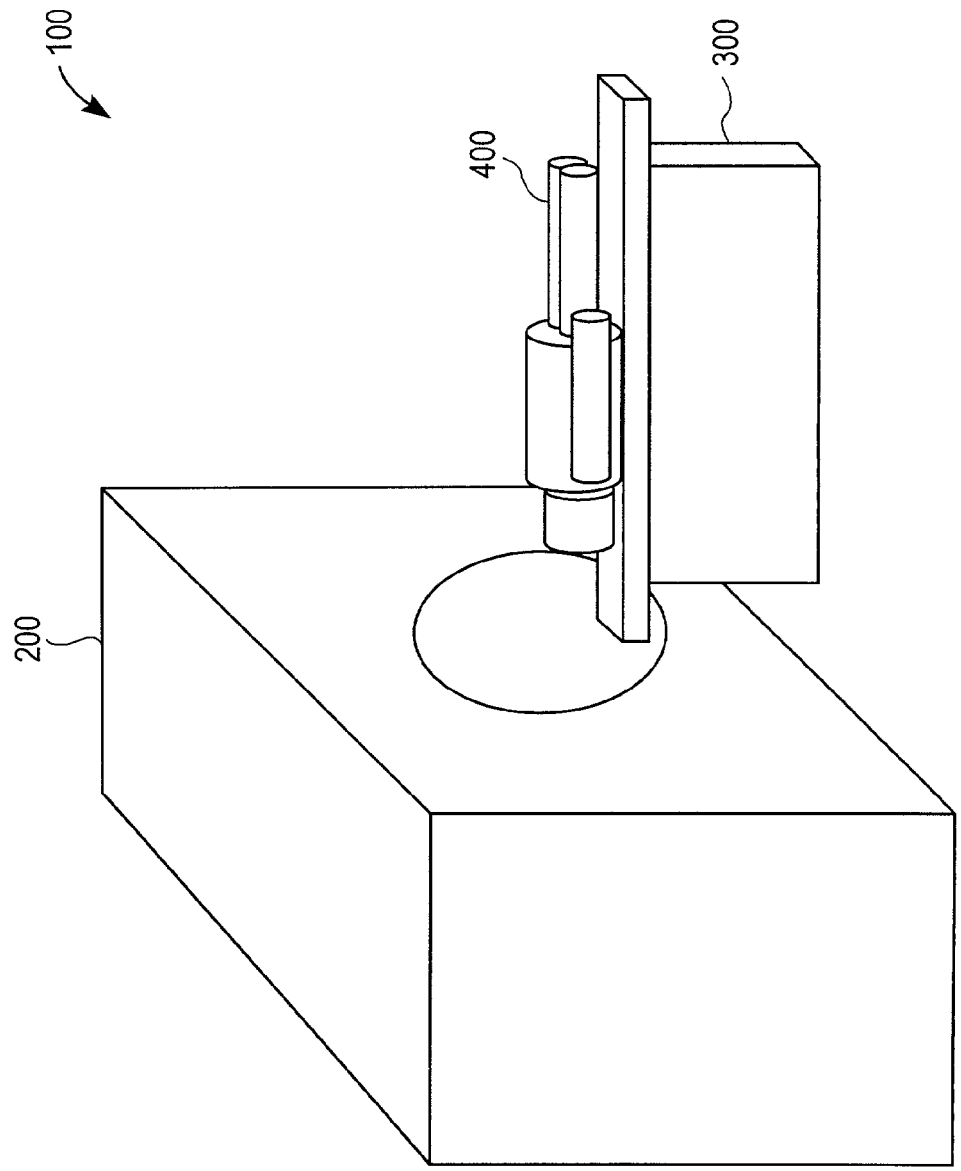
FIG. 1 shows a diagram of a computed tomography device.

Turning now to the drawings, FIG. 1 illustrates computed tomography ("CT") room 100 configured to acquire data in accordance with some embodiments of the present invention. CT room 100 includes CT device 200, CT table 300, and object 400. CT device 200 is used to obtain CT data representing at least a portion of object 400. Specifically, CT device acquires CT data by exploiting the x-ray principle: as x-rays pass through the body they are absorbed or attenuated at differing levels, thereby creating a matrix or profile of x-ray beams of different strength. In conventional x-ray imaging, an image of the profile is produced using film that is sensitive to x-rays. In the case of CT, the film is replaced by a banana-shaped detector that measures the x-ray profile and outputs data representing the profile.

The detector is mounted on a rotating frame inside CT device 200. Mounted opposite to the detector is an x-ray tube that emits a fan beam of x-rays as the rotating frame spins the x-ray tube and detector around object 400. As the x-ray tube and detector spin, the detector measures profiles of the attenuated x-ray beam. Typically, in one 360° spin, about 1,000 profiles are measured. Each profile is subdivided spatially by the detector and fed into about 700 individual data channels. Each profile is then reconstructed into a two-dimensional image of the portion or "slice" that was scanned. The two-dimensional images may be processed to create a three-dimensional image. Both the two-dimensional images and the three-dimensional image are referred to herein as CT data, and both show tissue as well as bone.

The physician will use the CT data to anatomically reconstruct the object 400 and determine the dosage goals. The dosage may be prescribed in centigrays (cGy). A physician may also use other types of reconstruction methods known to one of ordinary skill in the art to determine the dosage goals. The treatment area, or field, may be divided into segments where each segment is to receive a different amount of radiation.

CT table 300 is used to position an object before, during and after acquisition of CT data. As such, CT table 300 is capable of moving so as to place relevant portions of the object 400 in the path of the x-ray beam within CT device 200. This movement may be under the control of an operator and/or a computer program. It should be noted that any currently or hereafter-known CT table and CT device may be used in accordance with the present invention.

Figure 2:
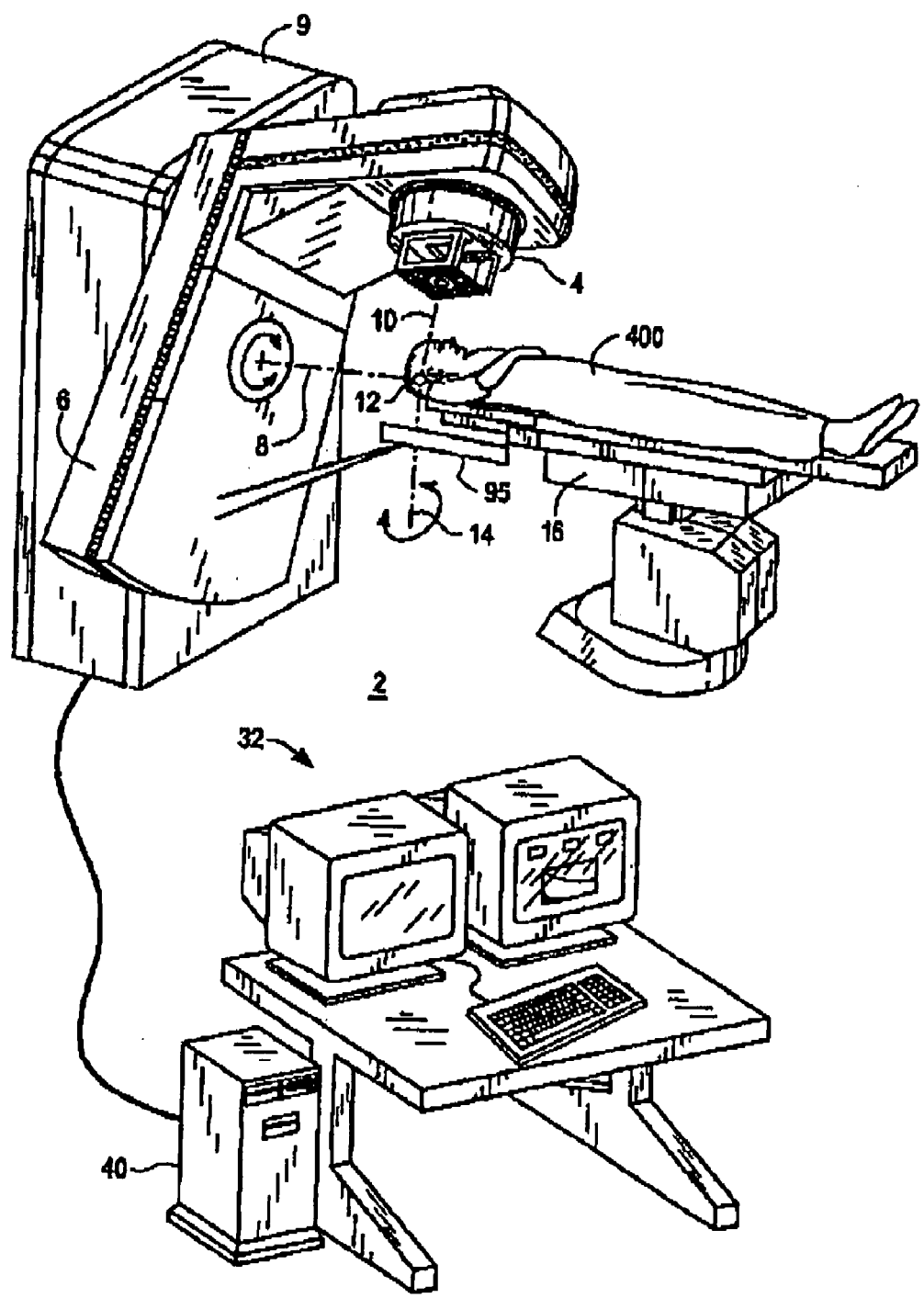
FIG. 2 shows a diagram of a radiation treatment device including a treatment console constructed in accordance with the invention.

FIG. 2 shows a radiation treatment device 2 of common design. Radiation device 2 includes plates or leaves 4, a control unit in a housing 9, and a gantry 6. Plates 4 are fastened to a projection of gantry 6. Gantry 6 can be swiveled around a horizontal axis of rotation 8 during therapeutic treatment. To generate the high-powered radiation required for therapy, a linear accelerator is located within gantry 6. The axis of the radiation bundle emitted from the linear accelerator and gantry 6 is designated by 10. Electron, photon, or any other detectable radiation can be used for the therapy.

Radiation treatment device 2 also includes treatment unit 32 which is usually located apart from gantry 6 and treatment table 16. Preferably, the radiation treatment device 2 is located in a different room from treatment unit 32 to protect the therapist from radiation exposure.

Referring back to FIG. 2, during treatment, the radiation beam is focused on a zone 12 of an object 400 (e.g., a patient who is to be treated, and who lies at the isocenter of the gantry rotation). The rotational axis 8 of gantry 6, the rotational axis 14 of the area to be treated, and the beam axis 10 all preferably intersect in the isocenter of zone 12. The construction of such a radiation treatment device is described in general in a brochure "Digital Systems for Radiation Oncology", Siemens Medical Laboratories, Inc. A91004-M2630-B358-01-4A00, September 1991.

During the treatment the radiation beam is trained on a zone 12 of an object 400, for example, a patient that is to be treated, and who lies at the isocenter of the gantry rotation. The rotational axis 8 of gantry 6 and the rotational axis 14 of a treatment table 16, and the beam axis 10 all preferably intersect at the isocenter.

Treatment unit 32 includes an output device, such as a visual display unit or monitor 70, and a keyboard 19. Treatment unit 32 is routinely operated by a therapist who administers delivery of a radiation treatment as prescribed by an oncologist. The treatment unit includes a central processing unit (CPU) 18. By utilizing keyboard 19, the therapist can program treatment unit 32, so that the prescribed radiation is delivered to the object. The program can also be input via another input device such as a data storage device located within the central processing unit (CPU) 18 or through data transmission to CPU 18.

A control unit 40 receives position information from gantry 6, and it receives information about radiation emission from measuring chamber 91. Detector array 95 provides exit radiation signals 89 to control unit 40. These exit radiation signals 89 include information about the amount of radiation which has passed through object 400.

Figure 3:
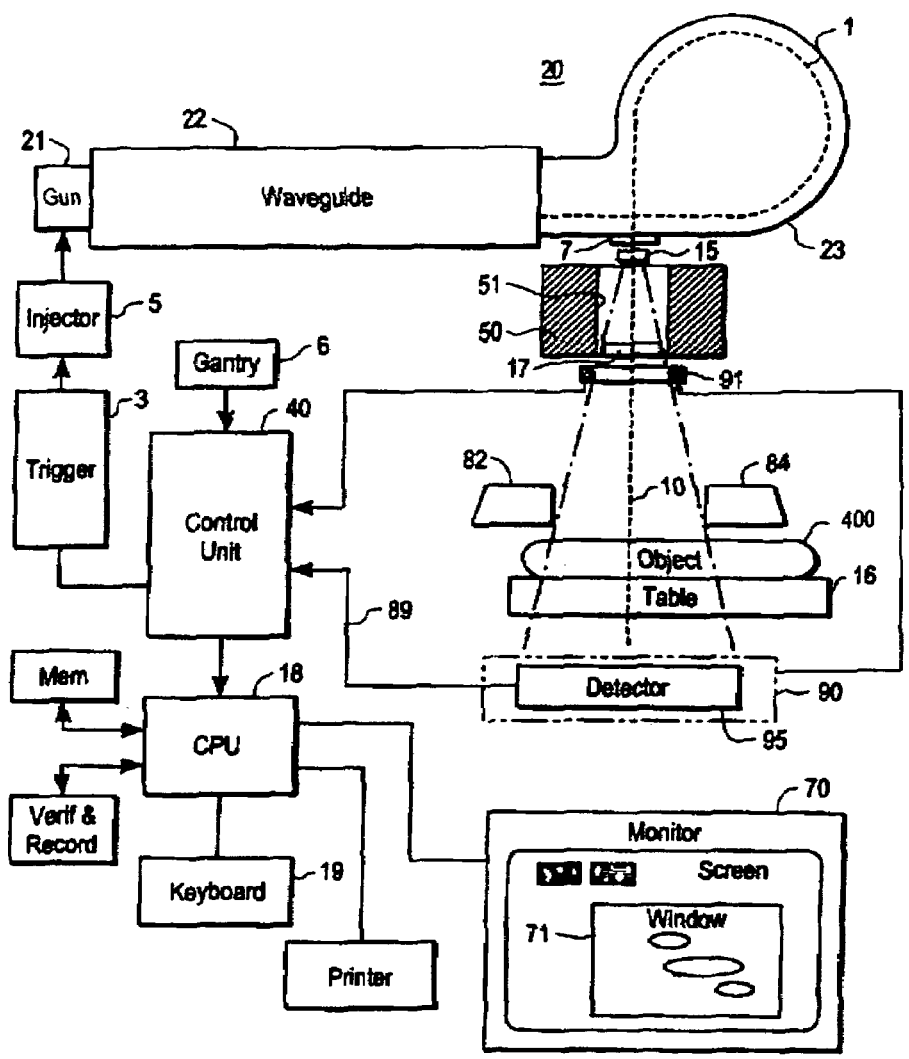
FIG. 3 is a block diagram illustrating portions of a processing unit, a control unit, and a beam generation system in the radiation treatment device of FIG. 2.

FIG. 3 shows portions of radiation treatment device 2 and portions of treatment unit 32 in more detail. An electron beam 1 (also referred to as a radiation beam) is generated in an electron accelerator 20. Accelerator 20 includes an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters guide magnet 23, and from there is guided through a window 7 along axis 10. After passing through a first scattering foil 15, the beam goes through a passageway 51 of a shield block 50 and encounters a second scattering foil 17.

Figure 4:
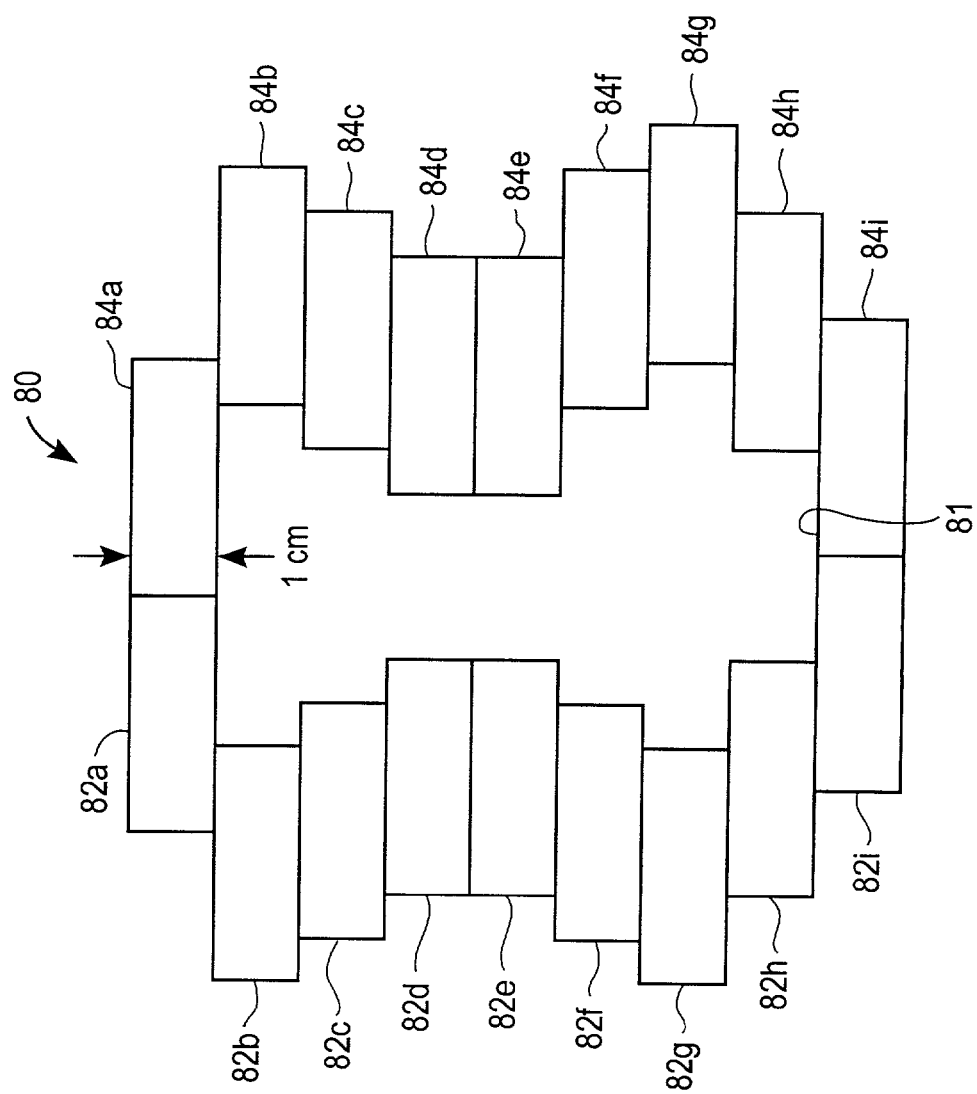
FIG. 4 is a schematic illustrating the leavees of a multi-leaf collimator positioned for treatment in the radiation treatment device of FIG. 2.

Next, the dose is ascertained by a first detector array 91 located above the object 400. The area of the object that is irradiated is sometimes referred to as the "field". FIG. 4 illustrates a beam shielding device, generally indicated at 80. The beam shielding device is provided in the path of the beam 1 to define a radiation field 81, and includes a plurality of opposing plates or leaves 82a-i and 84a-i, only two of which are shown in FIG. 3 for simplification. FIG. 4 illustrates leaves 82a-i and 84a-i (forming leaf pairs 82a and 84a, 82b and 84b, . . . , 82i and 84i) of a multi-leaf collimator mounted between the radiation source and object positioned to define a treatment field by delimiting the electron beam 1 to more accurately irradiate the field. Leaves 82 and 84 are substantially impervious to emitted radiation. Areas of the body outside the field (e.g., healthy tissue) are therefore subjected to as little radiation as possible, and preferably to none at all.

The leaves 82a-i, 84a-i typically have a one centimeter width and are substantially impervious to the emitted radiation so that they block healthy tissue from the radiation. As is described above, this is just one example of a beam-shielding arrangement that can be used in the present invention.

Moreover, plates, although common, are not the only type of beam-shielding devices available. For example, most radiation devices contain some form of beam collimator, wedge, compensator, jaw and/or other aperture device. Thus, the aperture device itself can act as the beam-shielding device, and the various beam-shielding devices can be combined to limit the delivered radiation. The present invention can be used with any such arrangement. The invention can be used in dynamic conformal treatments during which the gantry, collimator, jaws and multileaf collimators could all be in motion during the radiation distribution. Furthermore, the gantry can be rotated to allow different beam angles and radiation distributions without having to move the object. The present invention can also be used with fixed-field devices (i.e., no movable plates), with constant radiation delivery rates, and with fixed-angle beams (i.e., no rotatable gantry).

The system may include a second detector array 95 located below the object from the viewpoint of the beam source. In some embodiments, each of the first and second detector arrays may be a two-dimensional array. One example of such a detector is the 2-D array provided by the German company PTW Freiburg which manufactures a 2-D Array for IMRT which consists of a 16×16 matrix. However, this is just one example of a detector array, and one of ordinary skill in the art would appreciate that other types of detectors may also be used.

The first detector array 91 controls the linac by instructing the control unit to turn the beam on and off (the "reference array"). The amount of the radiation beam delivered to object 13 is measured by the second detector array 95 such that radiation is sensed after it has passed through object 13. The second detector array may be comprised of detectors that measure the delivered dosage to each pixel of the targeted segment.

The second detector array 95 measures the actual radiation delivered to object 13 with the assistance of a Monte Carlo algorithm. Monte Carlo methods follow basic principles of physics and simulate the paths and interactions of individual particles (e.g., photons/electrons) in the radiation beam as they travel through the linac delivery system and the object. This simulation provides estimates of the radiation transport and deposition during a treatment. The Monte Carlo algorithm may also be used to calculate other items of interest such as, but not limited to, the combination of gantry positions, collimator settings, and segments per field.

Figure 5:
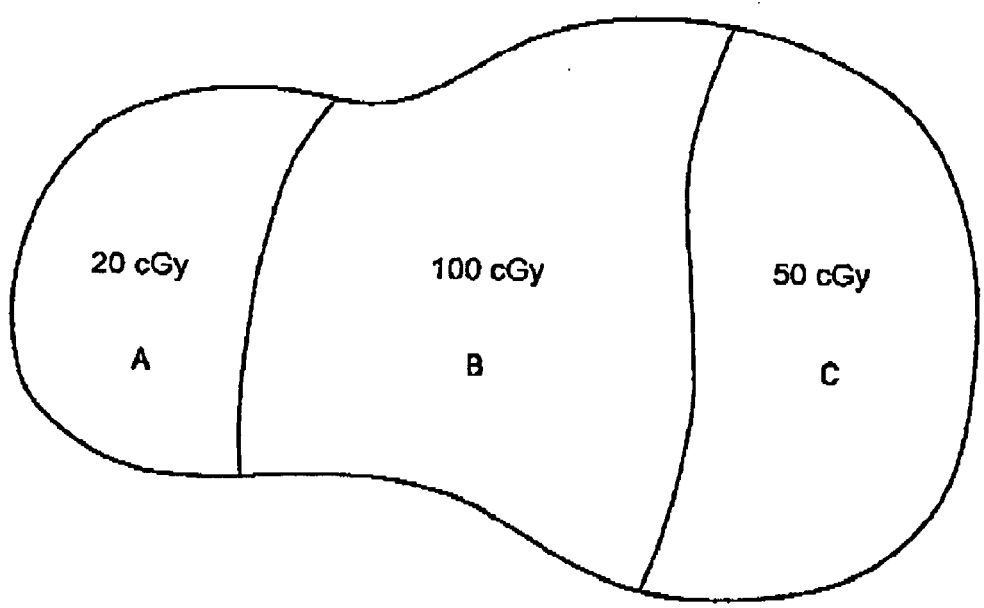
FIG. 5 is a diagram showing an example of a treatment field divided into three segments.

The control unit may be programmed to automatically shut off once the prescribed dose is delivered. Alternatively, the second detector array 95 may communicate the exit dosage information to the control unit to control the leaves of the multileaf collimator to conform to the shape of the segment of the treatment field prescribed by the physician. FIG. 5 illustrates an example treatment field divided into three segments in which each segment has been prescribed a different radiation dosage. In this example, the physician has divided the treatment field into three separate segments A, B, and C. Segment A is prescribed 20 cGy, segment B is prescribed 100 cGy, and segment C is prescribed 50 cGy. As discussed previously, the physician determines the dose goals based on anatomical reconstruction of the object acquired from the CT data. Accordingly, the control unit directs the leaves of the multileaf collimator to initially shield segments B and C so that the radiation is delivered to segment A only. The second detector array measures the radiation delivered to segment A. Once 20 cGy are delivered to segment A, the second detector array communicates to first detector array to shut off the radiation beam. Afterwards, the leaves are positioned to shield segments A and C so that 100 cGy may be delivered to segment B. Likewise the same process occurs for the treatment of segment C.

The second detector array 95 may also provide the source of data used to correlate each data set to correct errors in the dose being delivered and/or object positioning. For example, if the object were not receiving the prescribed dosage, the beam would remain on until the correct level is attained.

In some embodiments, using the exit dose information (e.g., the angle of the incidence beam, thickness of the object, and distance and angle of the exit beam) in a virtual detection-reconstruction method, the CPU may reconstruct a dosage map segment by segment. In one embodiment of the present invention, the exit dose is displayed on the screen of monitor 70 in a display area 71. Various other data can also be displayed before, during and after treatment on monitor 70. Instead of or in addition to monitor 70, other output devices, such as a printer, can be utilized.

What is claimed is:

1. A system for delivering radiation to an object, the system comprising:
   a radiation source to generate an output beam directed to an object;
   a multi-leaf collimator mounted between the radiation source and the object, the multi-leaf collimator to define a first predetermined irradiation field of the object;
   a control unit configured to control the radiation source and the multi-leaf collimator;
   a first radiation detector array comprising a first matrix of ion chambers to measure a radiation dosage delivered to each ion chamber of the first matrix and to instruct the control unit to turn the output beam off; and
   a second detector array comprising a second matrix of ion chambers to measure a radiation dosage delivered to the first predetermined irradiation field, and configured to communicate to the first radiation detector array to turn the output beam off,
   wherein, in response to the communication to turn the output beam off, the control unit is configured to control the multi-leaf collimator to be repositioned to define a second predetermined irradiation field of the object and the control unit is configured to control the radiation source to generate an output beam directed to the second predetermined irradiation field.

2. The system of claim 1, wherein the second detector array is an element of a portal imaging system, and wherein the object is disposed between the radiation source and the portal imaging system.

3. The system of claim 1, the control unit to determine an amount of radiation delivered to different portions of the object based on the radiation dosage delivered to each ion chamber of the second matrix and on a Monte Carlo algorithm.

4. A method for delivering radiation to an object, the method comprising the steps of:
   using a radiation beam to deliver radiation to an object;
   using a first radiation detector to detect the radiation beam before the radiation beam reaches the object;
   using a second radiation, detector array comprising a matrix of ion chambers to measure a radiation dosage delivered to a first predetermined irradiation field, and to communicate to the first radiation detector to turn the radiation beam off;
   turning the radiation beam off in response to an instruction to turn the radiation beam off received from the first radiation detector;
   repositioning a multi-leaf collimator to define a second predetermined irradiation field of the object in response to the instruction to turn the radiation beam off; and
   using the radiation source to deliver second radiation to the second predetermined irradiation field of object.

* * * * *